(12) United States Patent
Watanabe et al.

(10) Patent No.: US 9,931,091 B2
(45) Date of Patent: Apr. 3, 2018

(54) DOSE DISTRIBUTION DISPLAY APPARATUS AND AN X-RAY DIAGNOSTIC APPARATUS

(71) Applicant: Toshiba Medical Systems Corporation, Otawara (JP)

(72) Inventors: Yuichiro Watanabe, Yaita (JP); Takuya Sakaguchi, Utsunomiya (JP); Yoshinori Shimizu, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 205 days.

(21) Appl. No.: 14/919,082

(22) Filed: Oct. 21, 2015

(65) Prior Publication Data
US 2016/0151031 A1   Jun. 2, 2016

(30) Foreign Application Priority Data

Nov. 28, 2014 (JP) .................................. 2014-242259
Sep. 29, 2015 (JP) .................................. 2015-191264

(51) Int. Cl.
*H05G 1/64* (2006.01)
*A61B 6/00* (2006.01)

(52) U.S. Cl.
CPC ............ *A61B 6/463* (2013.01); *A61B 6/4441* (2013.01); *A61B 6/487* (2013.01); *A61B 6/5294* (2013.01); *A61B 6/542* (2013.01)

(58) Field of Classification Search
CPC ...... A61B 6/542; A61B 6/4014; A61B 6/4441; A61B 6/463; G06T 11/60; G09G 5/377; G09G 2340/12; G09G 2380/08; G01N 23/04

See application file for complete search history.

(56) References Cited

U.S. PATENT DOCUMENTS

| | | | |
|---|---|---|---|
| 8,611,499 B2 | 12/2013 | Spahn | |
| 8,681,941 B2 | 3/2014 | Bernhardt et al. | |
| 9,655,585 B2 * | 5/2017 | Watanabe | A61B 6/542 |

* cited by examiner

*Primary Examiner* — Courtney Thomas
(74) *Attorney, Agent, or Firm* — Oblon, McClelland, Maier & Neustadt, L.L.P.

(57) ABSTRACT

According to one embodiment, a dose distribution display apparatus includes storage circuitry, processing circuitry, and display circuitry. The storage circuitry stores position information of a support frame which supports an X-ray tube, and X-ray information concerning X-rays generated by the X-ray tube. The processing circuitry edits at least one of the X-ray information and the position information in accordance with an operator instruction, and generates a plurality of simulated dose distributions in time series based on the X-ray information and the position information, at least one of which has been edited, The display circuitry sequentially superimposes and displays the simulated dose distributions on an object model.

7 Claims, 12 Drawing Sheets

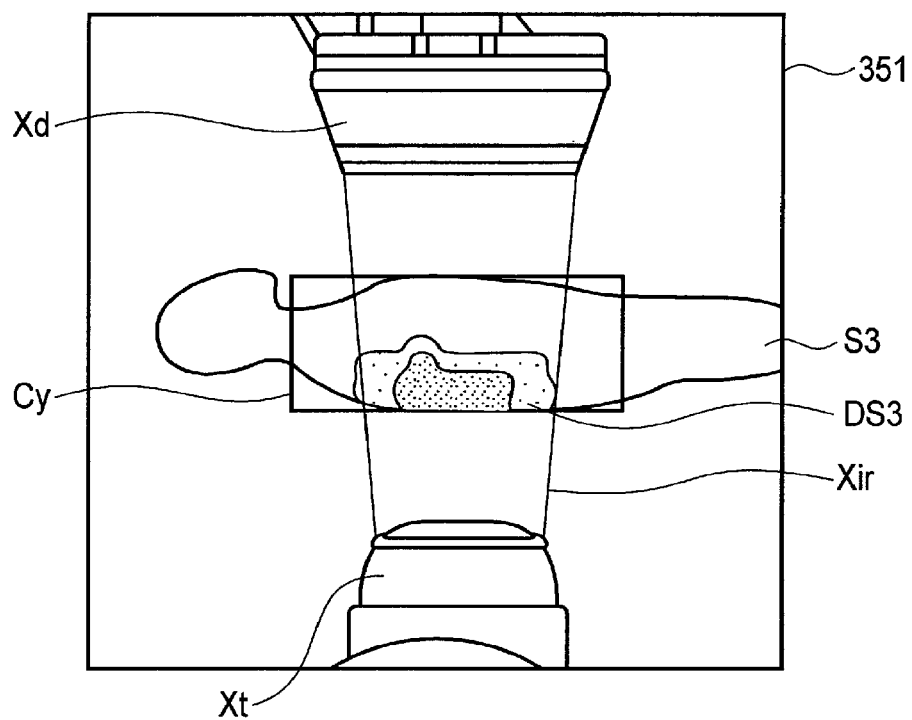
F I G. 4

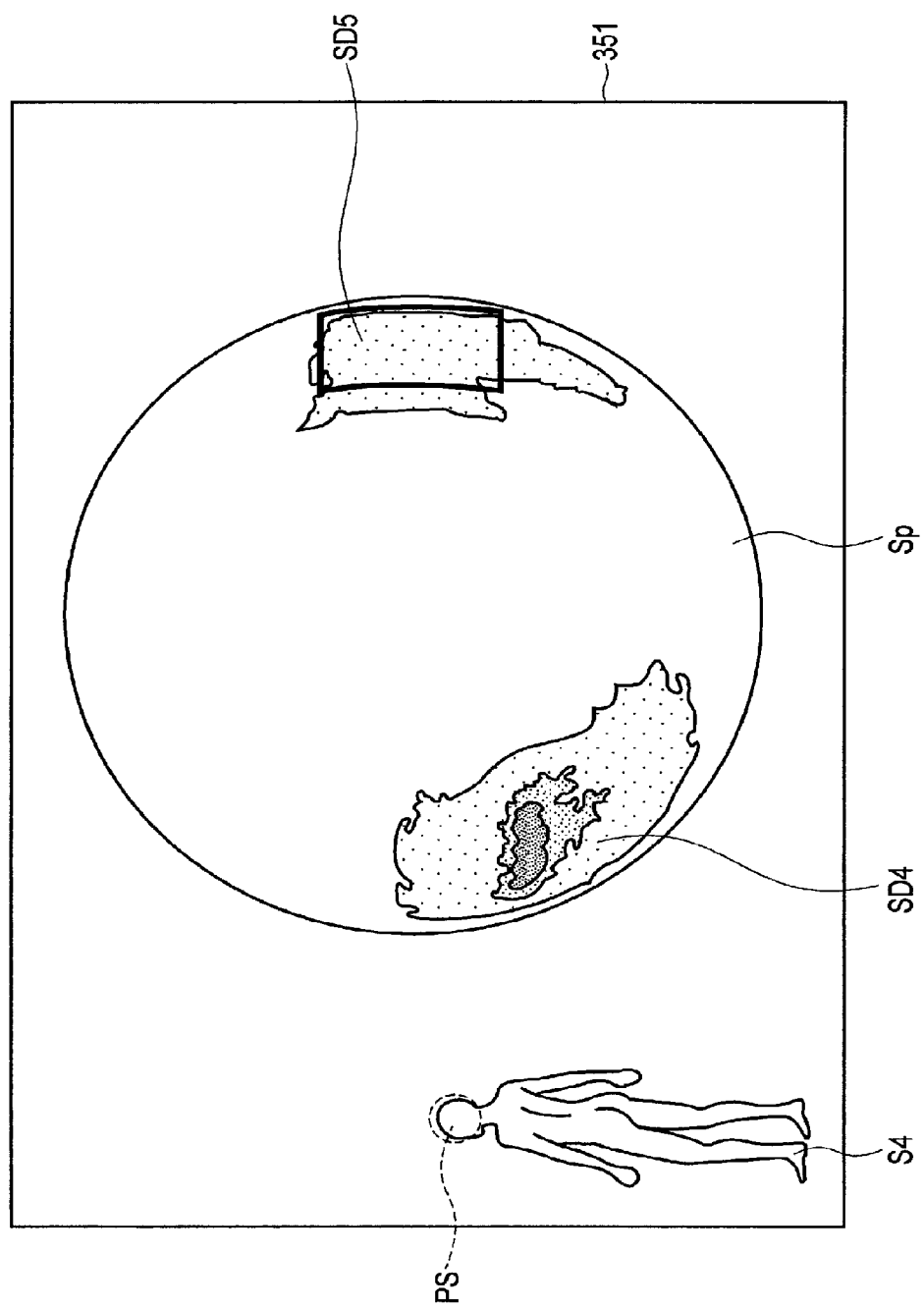
F I G. 5

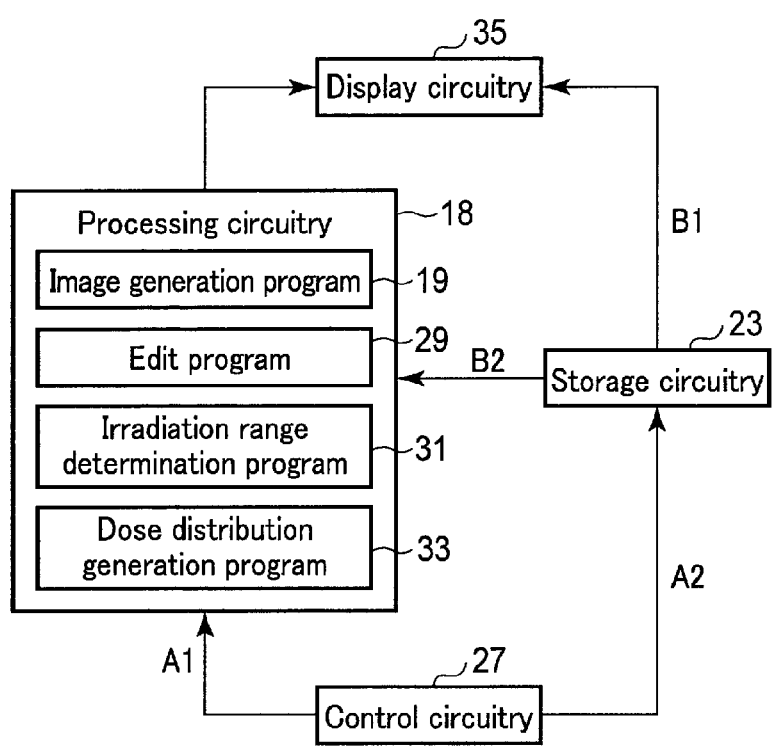
F I G. 6

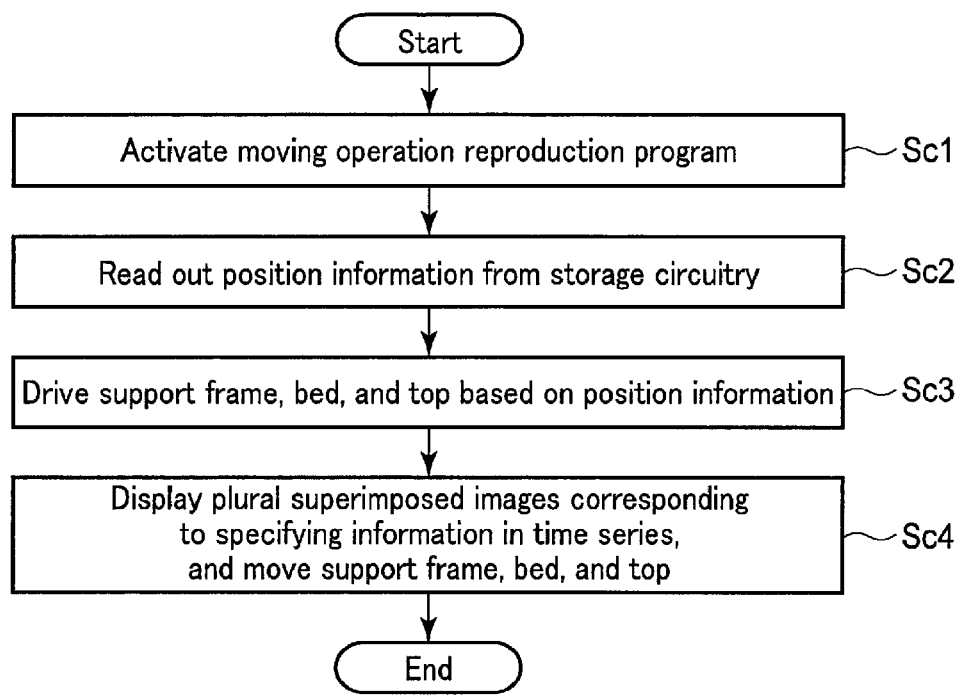
F I G. 11

DOSE DISTRIBUTION DISPLAY APPARATUS AND AN X-RAY DIAGNOSTIC APPARATUS

CROSS-REFERENCE TO RELATED APPLICATIONS

This application is based upon and claims the benefit of priority from the prior Japanese Patent Application No. 2014-242259, filed Nov. 28, 2014 and the prior Japanese Patent Application No. 2015-191264, filed Sep. 29, 2015, the entire contents all of which are incorporated herein by reference.

FIELD

Embodiments described herein relate generally to a dose distribution display apparatus and an x-ray diagnostic apparatus able to generate a simulated dose distributions for an object.

BACKGROUND

There is a function of displaying a skin exposure distribution dose on an object in real time during execution of an X-ray examination (e.g., interventional radiology: IVR).

BRIEF DESCRIPTION OF THE DRAWINGS

FIG. 4 is a view showing an example of a simulated dose distribution displayed on the display together with a cylindrical dose distribution display model according to this embodiment.

FIG. 5 is a view showing an example of a simulated dose distribution displayed on the display together with a spherical dose distribution display model according to this embodiment.

FIG. 6 is a block diagram showing the association between circuits regarding a simulated dose distribution generation display function according to this embodiment.

FIG. 11 is a flowchart showing an example of a procedure for moving operation reproduction processing according to the first modification of this embodiment.

DETAILED DESCRIPTION

Figure 1:
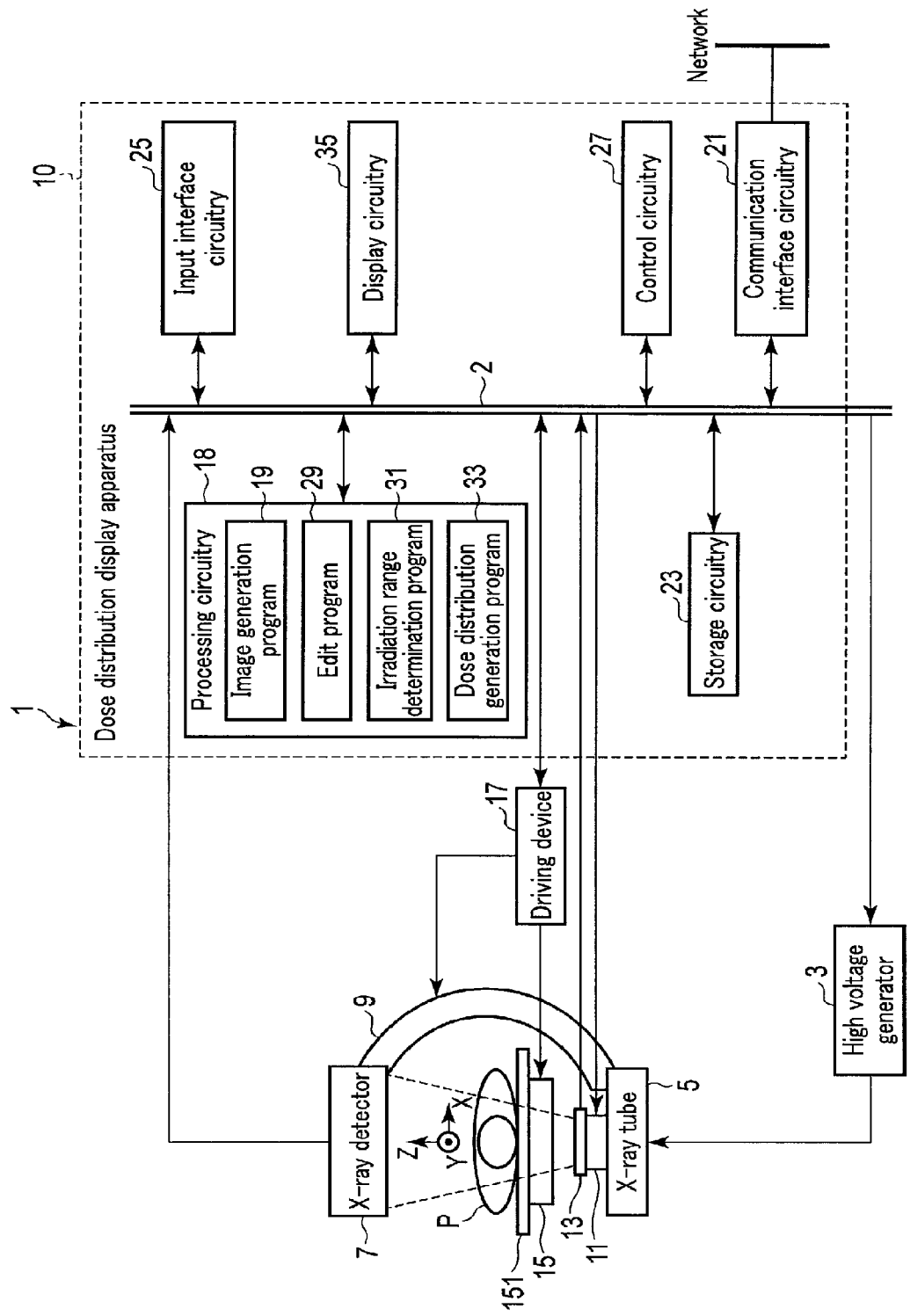
FIG. 1 is a block diagram showing an example of the arrangement of an X-ray diagnostic apparatus according to an embodiment.

In general, according to one embodiment, a dose distribution display apparatus includes storage circuitry, processing circuitry, and display circuitry. The storage circuitry stores position information of a support frame which supports an X-ray tube, and X-ray information concerning X-rays generated by the X-ray tube. The processing circuitry edits at least one of the X-ray information and the position information in accordance with an operator instruction, and generates a plurality of simulated dose distributions in time series based on the X-ray information and the position information, at least one of which has been edited, The display circuitry sequentially superimposes and displays the simulated dose distributions on an object model.

An X-ray diagnostic apparatus according to an embodiment will be described below with reference to the accompanying drawing. Note that the same reference numerals in the following description denote constituent elements having almost the same functions and arrangements, and a repetitive description will be made only when required.

FIG. 1 is a block diagram showing the hardware arrangement of an X-ray diagnostic apparatus 1 according to this embodiment. The X-ray diagnostic apparatus 1 includes a bus (data bus) 2, a high voltage generator 3, an X-ray tube 5, an X-ray detector 7, a support frame 9, an irradiation range limiter (X-ray stop) 11, a dosimeter 13, a bed 15 including a top plate 151, a driving device 17, processing circuitry 18, communication interface circuitry 21, storage circuitry (storage unit) 23, input interface circuitry (input unit) 25, control circuitry (control unit) 27, and display circuitry (display unit) 35.

The bus 2 is, for example, a signal path which connects the high voltage generator 3, the X-ray detector 7, the irradiation range limiter (X-ray stop) 11, the dosimeter 13, the driving device 17, the processing circuitry 18, the communication interface circuitry 21, the storage circuitry 23, the input interface circuitry 25, the control circuitry 27, and the display circuitry 35.

Figure 2:
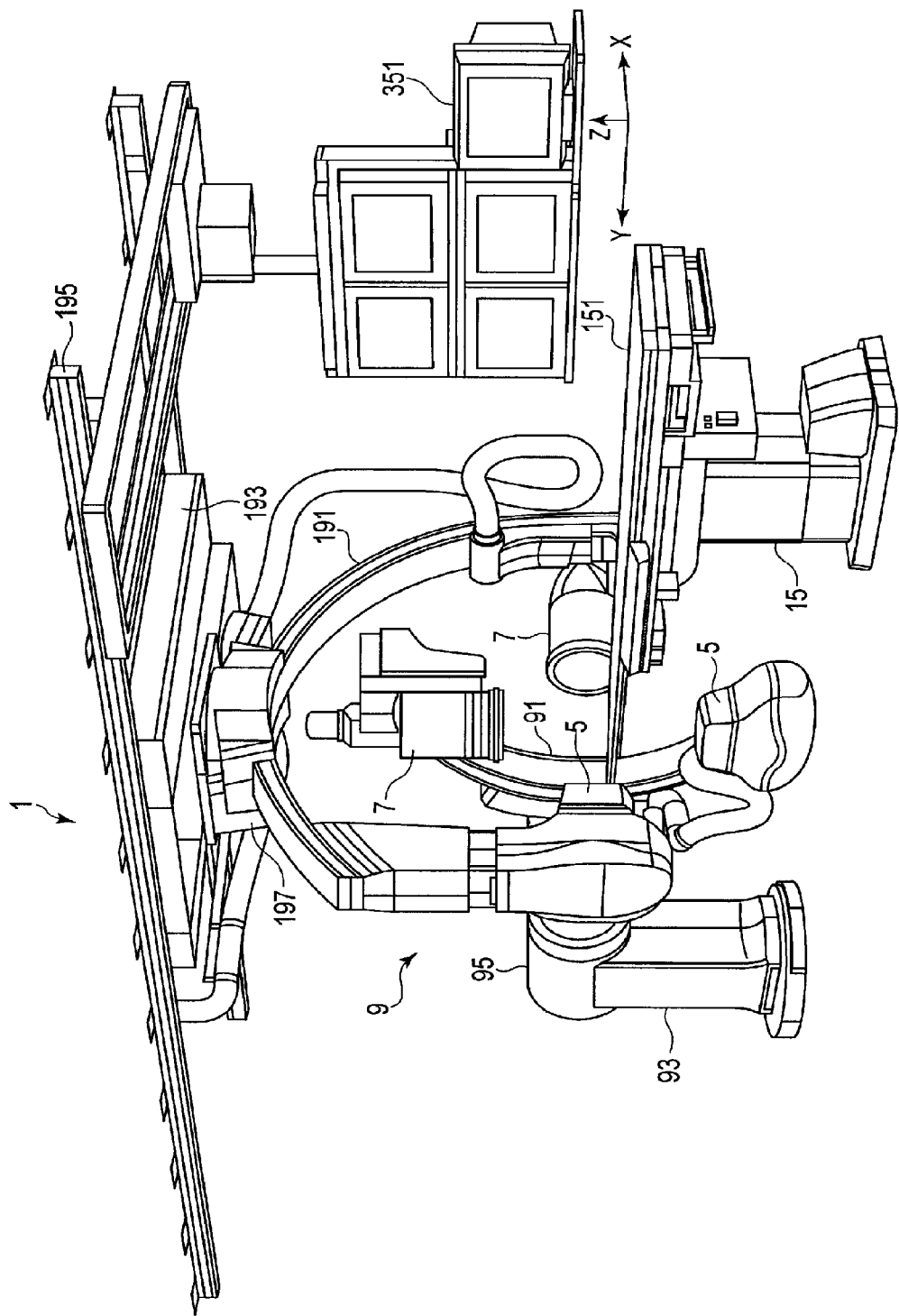
FIG. 2 is a perspective view showing the outer appearance of the X-ray diagnostic apparatus according to this embodiment.

FIG. 2 is a perspective view showing the outer appearance of the X-ray diagnostic apparatus 1 according to this embodiment.

The high voltage generator 3 generates a tube current to be supplied to the X-ray tube 5 and a tube voltage to be applied to the X-ray tube 5. The high voltage generator 3 supplies tube currents respectively suited to X-ray imaging and X-ray fluoroscopy to the X-ray tube 5, and applies tube voltages respectively suited to X-ray imaging and X-ray fluoroscopy to the X-ray tube 5 in accordance with X-ray irradiation conditions (to be described later) under the control of the control circuitry 27 (to be described later). The X-ray irradiation conditions are, for example, the tube current, the tube voltage, the irradiation time, and the product (to be referred to as a "tube current time product (mAs) hereinafter) of the tube current (mA) and irradiation time (s) for each X-ray irradiation.

The X-ray tube 5 generates X-rays from an X-ray focus (to be referred to as a tube focus hereinafter) based on the tube current supplied from the high voltage generator 3 and the tube voltage applied by the high voltage generator 3. The X-rays generated from the tube focus irradiate an object P through an X-ray radiation window provided on the front surface of the X-ray tube 5.

The X-ray detector 7 detects the X-rays which have been generated from the X-ray tube 5 and have passed through the object P. For example, the X-ray detector 7 includes a flat panel detector (to be referred to as an FPD hereinafter). The FPD includes a plurality of semiconductor detection elements. Semiconductor detection elements are classified into a direct conversion type and an indirect conversion type. The direct conversion type is a scheme of directly converting incident X-rays into an electrical signal. The indirect conversion type is a scheme of converting incident X-rays into light through a phosphor and converting the light into an electrical signal. An image intensifier may be used as the X-ray detector 7.

The electrical signal generated by a plurality of semiconductor detection elements upon incidence of the X-rays is output to an analog to digital converter (to be referred to as an A/D converter hereinafter) (not shown). The A/D converter converts an electrical signal into digital data. The A/D converter outputs the digital data to the preprocessing unit (not shown) of the processing circuitry 18.

The support frame 9 movably supports the X-ray tube 5 and the X-ray detector 7. More specifically, the support frame 9 includes, for example, a C-arm 91 and a C-arm support member 93 in FIG. 2. The X-ray tube 5 and the X-ray detector 7 are mounted on the C-arm 91 so as to face each other. An Ω-arm 97 may be used instead of the C-arm 91. The C-arm support member 93 supports the C-arm 91 so that the C-arm 91 can slide in a direction (to be referred to as a first direction hereinafter) along the C shape of the C-arm via a guide rail, a linear motion bearing, and the like.

The C-arm support member 93 supports the C-arm 91 so that the C-arm 91 can rotate almost about a C-arm connecting member 95, which connects the C-arm 91 to the C-arm support member 93, in a direction (to be referred to as a second direction hereinafter) perpendicular to the first direction via a bearing and the like.

Note that the C-arm support member 93 can also support the C-arm 91 so that the C-arm 91 can be translated in the short-axis direction (X direction in FIGS. 1 and 2) and long-axis direction (Y direction in FIGS. 1 and 2) of the top plate 151 (to be described later) via a guide rail, a linear motion bearing, and the like. Also, the C-arm 91 supports the X-ray tube 5 and the X-ray detector 7 so that the distance (source image distance: to be referred to as an SID hereinafter) between the tube focus of the X-ray tube 5 and the X-ray detector 7 can be changed.

Note that the support frame 9 may further include an Ω-arm 191 and an Ω-arm support member 193, as shown in FIG. 2. The X-ray tube 5 and the X-ray detector 7 are mounted on the Ω-arm 191 so as to face each other. The Ω-arm support member 193 supports the Ω-arm 191 so that the Ω-arm 191 can slide in a direction (to be referred to as an Ω direction hereinafter) along the Ω-shape of the Ω-arm 191 via a guide rail, a linear motion bearing, and the like.

At this time, the Ω-arm support member 193 is installed movably along rails 195 provided on the ceiling via a linear motion bearing and the like. The rails 195 are provided on the ceiling so as to be parallel to, for example, the long-axis direction of the top plate 151. The Ω-arm support member 193 supports the Ω-arm 191 so that the Ω-arm 191 can rotate almost about an Ω-arm connecting member 197, which connects the Ω-arm 191 to the Ω-arm support member 193 via a bearing and the like, in a direction (to be referred to as an Ω orthogonal direction hereinafter) orthogonal to the Ω direction.

Note that the Ω-arm support member 193 can also support the Ω-arm 191 via a guide rail, a linear motion bearing, and the like so that the Ω-arm 191 can be translated in the short-axis direction (X direction in FIG. 2) and long-axis direction (Y direction in FIG. 2) of the top plate 151 (to be described later). In addition, the Ω-arm 191 supports the X-ray tube 5 and the X-ray detector 7 so that the distance (SID) between the tube focus and the X-ray detector 7 can be changed.

Note that the support frame 9 in the X-ray diagnostic apparatus 1 according to this embodiment is not limited to a structure implemented by the C-arm 91. The support frame 9 may be supported movably in an arbitrary direction by two arms (e.g., robot arms) which support, for example, the X-ray tube 5 and the X-ray detector 7, respectively.

The support frame 9 may be the Ω-arm 97 suspended from the ceiling, instead of the C-arm 91. The support frame 9 may have a biplane structure. The support frame 9 in the X-ray diagnostic apparatus 1 according to this embodiment is not limited to an over tube system, under tube system, or the like, and is applicable to an arbitrary form.

The irradiation range limiter 11 is provided on the front surface of the X-ray radiation window of the X-ray tube 5. That is, the irradiation range limiter 11 is provided between the X-ray tube 5 and the X-ray detector 7. The irradiation range limiter 11 is also called an X-ray movable stop.

More specifically, the irradiation range limiter 11 limits an irradiation range having a maximum aperture in accordance with an irradiation area by which the body surface of the object P is irradiated with X-rays, in order to prevent unnecessary exposure of a region, other than an imaging region desired by an operator, to X-rays generated at the tube focus. For example, the irradiation range limiter 11 limits the irradiation range by moving aperture blades under the control of the control circuitry 27 in accordance with an irradiation range limiting instruction input via the input interface circuitry 25 (to be described later).

More specifically, the irradiation range limiter 11 includes a plurality of first aperture blades movable in a predetermined direction, and a plurality of second aperture blades movable in a direction different from the predetermined direction. The first and second aperture blades are made of lead which shields X-rays generated at the tube focus.

Note that the irradiation range limiter 11 may include a plurality of predetermined filters (to be referred to as radiation quality adjustment filters hereinafter) which are inserted into an X-ray irradiation field, in order to reduce the exposure dose to the object P and improve the image quality. The respective radiation quality adjustment filters have different thicknesses. Note that the respective radiation quality adjustment filters may be made of different materials and have the same thickness. The radiation quality adjustment filters change the radiation quality of X-rays generated at the tube focus in accordance with the thickness. The radiation quality adjustment filters are made of aluminum, copper, or the like.

The operator selects a radiation quality adjustment filter via the input interface circuitry 25 in accordance with an imaging plan for the object P. The radiation quality adjustment filter selected from the plurality of radiation quality adjustment filters is inserted into the X-ray irradiation field in the irradiation range limiter 11 under the control of the control circuitry 27 (to be described later). Note that the irradiation range limiter 11 may output, to the storage circuitry 23, the processing circuitry 18, and the like, the type of a radiation quality adjustment filter to be inserted into the X-ray irradiation field, and a limited irradiation range.

The radiation quality adjustment filters reduce, for example, low-energy X-ray components (soft radiation components) which are easily absorbed by the object P, out of X-rays (to be referred to as generated X-rays hereinafter) which are generated at the tube focus. Alternatively, the radiation quality adjustment filters may reduce, out of the generated X-rays, high-energy X-ray components which cause a decrease in the contrast of a medical image generated by an image generation program 19 (to be described later).

The dosimeter 13 is provided on the front surface of the irradiation range limiter 11. That is, the dosimeter 13 is provided between the X-ray detector 7 and the irradiation range limiter 11. The dosimeter 13 is, for example, an area dosimeter. The dosimeter 13 measures the integration value (area dose) of an area dose in a predetermined period.

The predetermined period is a dose measurement period. The dose measurement period corresponds to a readout period during which an area dose measured by the dosimeter 13 is read out from the dosimeter. The dosimeter 13 outputs an area dose read out for each readout period to the storage circuitry 23, the processing circuitry 18, and the like.

Note that the dosimeter 13 may not be mounted on the X-ray diagnostic apparatus 1. At this time, the storage circuitry 23 stores area doses measured in advance on the top plate 151 while changing X-ray irradiation conditions and the type (thickness) of a radiation quality adjustment filter. For example, the storage circuitry 23 stores the correspondence table (to be referred to as a dose correspondence table hereinafter) of an area dose corresponding to a tube voltage, a tube current time product, and the type (thickness) of a radiation quality adjustment filter.

The bed 15 includes the top plate 151 (also called a spine table) on which the object P is placed. The object P is placed on the top plate 151.

The driving device 17 drives the support frame 9 and the bed 15 under the control of the control circuitry 27. More specifically, the driving device 17 supplies a driving signal corresponding to a control signal from the control circuitry 27 to the C-arm support member 93 to slide the C-arm 91 in the first direction and rotate it in the second direction (CRA or CAU). Note that the driving device 17 may supply a driving signal corresponding to a control signal from the control circuitry 27 to the Ω-arm support member 193 to slide the Ω-arm 191 in the Ω direction and rotate it in the Ω orthogonal direction.

At the time of X-ray fluoroscopy and X-ray imaging, the object P placed on the top plate 151 is arranged between the X-ray tube 5 and the X-ray detector 7. The driving device 17 may rotate the X-ray detector 7 relative to the X-ray tube 5 under the control of the control circuitry 27. Note that the driving device 17 may output the position of the X-ray tube 5 (or the position of the support frame 9) relative to the top plate 151 and the rotational angle (to be referred to as an FPD rotational angle hereinafter) of the X-ray detector 7 to the storage circuitry 23, the processing circuitry 18, and the like.

The driving device 17 moves the top plate 151 by driving the top plate 151 under the control of the control circuitry 27. More specifically, the driving device 17 slides the top plate 151 in the short-axis direction (X direction in FIG. 1) of the top plate 151 or the long-axis direction (Y direction in FIG. 1) of the top plate 151 based on a control signal from the control circuitry 27.

The driving device 17 also moves the top plate 151 up and down in the vertical direction (Z direction in FIG. 1). In addition, the driving device 17 may rotate the top plate 151 to tilt it in at least either of the long-axis direction and short-axis direction as a rotation axis (X- or Y-axis in FIG. 1).

Note that the driving device 17 may output the position of the top plate 151 to the storage circuitry 23, the processing circuitry 18, and the like. Also, the driving device 17 may output the relative positional relationship between the X-ray tube 5 and the top plate 151 to the storage circuitry 23, the processing circuitry 18, and the like. The relative positional relationship between the X-ray tube 5 and the top plate 151 is, for example, the angles (tilts) of the C-arm 91 and Ω-arm 191 relative to the top plate 151, or the sliding angles (to be referred to as arm angles) of the C-arm 91 and Ω-arm 191. The tilt and the arm angle are Euler angles with reference to the isocenter relative to the object. Note that the driving device 17 may drive the X-ray detector 7 in order to arbitrarily rotate it in accordance with the position of the support frame 9, the angle of the C-arm 91 or Ω-arm 191, or the like.

The processing circuitry 18 is a processor which controls each circuitry and the like in the X-ray diagnostic apparatus 1. The processing circuitry 18 includes a CPU and a memory (neither is shown). The processing circuitry 18 reads out, from the storage circuitry 23, various programs for controlling each circuitry and the like in the X-ray diagnostic apparatus 1. The processing circuitry 18 loads the readout programs into its memory and executes them, implementing functions corresponding to the respective programs.

In other words, the processing circuitry 18 in a state in which the programs have been read out has functions such as the image generation function, an edit function, an irradiation range determination function, and a dose distribution generation function, as shown in FIG. 1. The image generation function, the edit function, the irradiation range determination function, and the dose distribution generation function will be described in detail later.

The processing circuitry 18 reads out a program (to be referred to as a preprocessing program hereinafter) corresponding to the preprocessing function from the storage circuitry 23, and executes the readout preprocessing program, implementing the preprocessing function (not shown). At this time, the processing circuitry 18 functions as a preprocessing unit.

The preprocessing function executes preprocessing on digital data output from the X-ray detector 7. Preprocessing includes correction of sensitivity unevenness between channels in the X-ray detector 7, and correction concerning an excessive decrease in signal or omission of data by an X-ray absorber such as metal. The image generation program 19 processes the preprocessed digital data.

The processing circuitry 18 reads out a program (to be referred to as an image generation program 19 hereinafter) corresponding to the image generation function from the storage circuitry 23, and executes the readout image generation program 19, implementing the image generation function. At this time, the processing circuitry 18 functions as an image generation unit.

The image generation program 19 generates a captured image based on digital data preprocessed after X-ray imaging at an imagining position. The image generation program 19 generates a fluoroscopic image based on digital data preprocessed after X-ray fluoroscopy at a fluoroscopy position. The captured image and the fluoroscopic image will be called projection images altogether. The image generation program 19 outputs the generated projection images to the storage circuitry 23 and the display circuitry 35.

The communication interface circuitry 21 is, for example, an interface concerning a network and an external storage device (not shown). Data such as projection images, analysis results, X-ray information/position information (to be described later), and the like obtained by the X-ray diagnostic apparatus 1 can be transferred to another apparatus via the communication interface circuitry 21 and the network.

The storage circuitry 23 is constituted by various memories, an HDD (Hard Disk Drive), an SSD (Solid State Drive), a magnetic disk (Floppy® disk, hard disk, or the like), an optical disk (CD-ROM, DVD, or the like), a semiconductor memory, and the like.

The storage circuitry 23 stores various programs such as the preprocessing program, the image generation program 19, an edit program 29 to be executed by the edit function of the processing circuitry 18, an irradiation range determination program 31 to be executed by the irradiation range determination function of the processing circuitry 18, and a dose distribution generation program 33 to be executed by the dose distribution generation function of the processing circuitry 18.

The storage circuitry 23 stores various X-ray images generated by the image generation program 19, control programs for the X-ray diagnostic apparatus 1, a diagnosis protocol, operator instructions sent from the input interface circuitry 25, various data groups such as imaging conditions and fluoroscopy conditions concerning X-ray imaging, various data sent via the communication interface circuitry 21 and a network, an area dose, a reference position, and the like. The reference position is, for example, a position spaced apart by a predetermined distance from the isocenter in the X-ray diagnostic apparatus 1 toward the focus of the X-ray tube 5. The storage circuitry 23 stores a dose correspondence table.

Note that the storage circuitry 23 may store a dose distribution generation display program. The dose distribution generation display program is a program which integrates the edit program 29, the irradiation range determination program 31, and the dose distribution generation program 33.

The storage circuitry 23 stores a plurality of object models as various models (called dose distribution display models) each representing the display region of a simulated dose distribution. The plurality of object models are, for example, a plurality of object models respectively corresponding to the sex, adult/child, overweight/standard weight/underweight, weight range, height range, and X-ray irradiation region.

Figure 3:
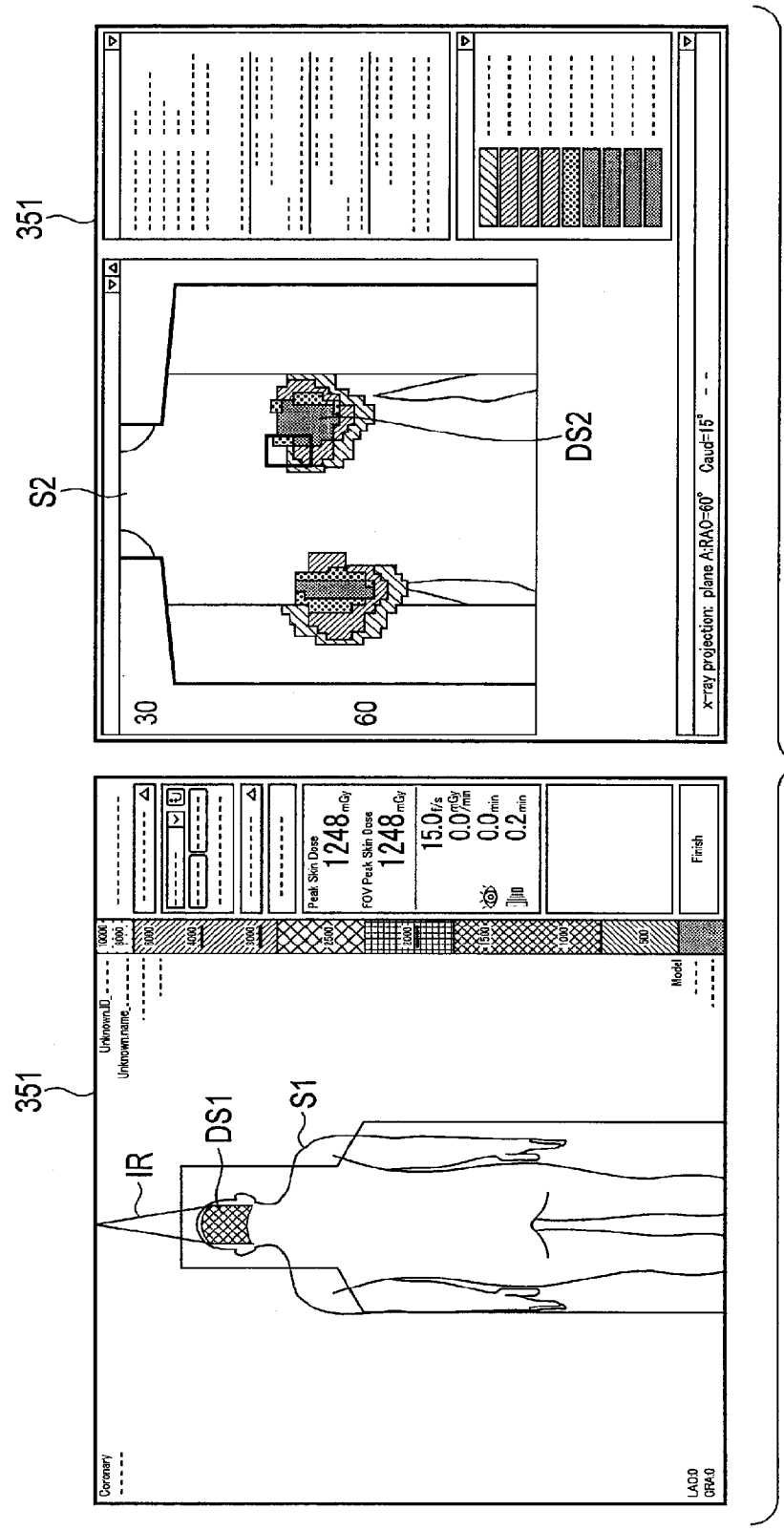
FIG. 3 is a view showing an example of an object model displayed on a display according to this embodiment.

S1 and S2 in FIG. 3 are views showing object models displayed on a display 351. IR in FIG. 3 represents the irradiation range of X-rays (X-ray irradiation range). DS1 in FIG. 3 represents a simulated dose distribution on the object model S1. DS2 in FIG. 3 represents a simulated dose distribution on the object model S2.

Note that the dose distribution display model displayed on the display 351 may have, for example, cylindrical shape as indicated by Cy in FIG. 4. The dose distribution display model is not limited to the cylindrical shape and may have an arbitrary three-dimensional shape (e.g., a cube, rectangular parallelepiped, or polyhedron). S3 in FIG. 4 is an object model concerning the cylindrical dose distribution display model.

When the dose distribution display model has a cylindrical shape, the storage circuitry 23 stores an X-ray detector model Xd, an X-ray tube model Xt, and an irradiation range Xir, as shown in FIG. 4. The irradiation range determination function 31 in the processing circuitry 18 determines the size of the irradiation range. DS3 in FIG. 4 represents a simulated dose distribution displayed on the cylindrical dose distribution display model.

The storage circuitry 23 may store a shape model corresponding to an imaging region as the dose distribution display model. For example, when the imaging region is the head region, a shape model corresponding to the imaging region is a spherical model. When the imaging region is the abdominal region, a shape corresponding to the imaging region is a columnar model.

FIG. 5 is a view showing an example of a shape model displayed on the display 351 when the imaging region is the head region. Sp in FIG. 5 represents a spherical model. SD4 and SD5 in FIG. 5 represent simulated dose distributions displayed on the spherical model. S4 in FIG. 5 is an object model for representing the region of the shape model. PS in FIG. 5 represents the position of the spherical model Sp in the object model S4.

The storage circuitry 23 stores in time series X-ray information output from the control circuitry 27 during an X-ray examination. The X-ray information is information concerning generation of X-rays in time series in the X-ray examination on an object. The X-ray information is, for example, information obtained by arraying in time series X-ray irradiation conditions, the type (thickness) of a radiation quality adjustment filter, a limited irradiation range, an area dose, and the like. Note that the type (thickness) of a radiation quality adjustment filter and a limited irradiation range in X-ray information may be input from the irradiation range limiter 11.

The storage circuitry 23 stores in time series geometrical position information output from the control circuitry 27 during an X-ray examination. The geometrical position information is information including the position of the top plate 151, the position of the C-arm 91, the angle of the C-arm 91, the SID, the FPD rotational angle, the relative positional relationship, and the like. Note that the geometrical position information may include a reference position. The geometrical position information in time series in the X-ray examination will be called position information. Note that the position information may be input from the driving device 17.

The storage circuitry 23 outputs position information, X-ray information, and an object model corresponding to specifying information to each predetermined circuitry under the control of the control circuitry 27. The specifying information is information for specifying X-ray information, position information, an object model, and the like. More specifically, the specifying information is information including, for example, the name and date & time of an X-ray examination, the name and ID of an object, and the weight and height of the object. The specifying information is input via the input interface circuitry 25 in accordance with an operator instruction.

The input interface circuitry 25 inputs X-ray irradiation conditions such as the imaging conditions of X-ray imaging and the fluoroscopy conditions of X-ray fluoroscopy desired by the operator, a fluoroscopy/imaging position, an irradiation range, and the like in accordance with an operator instruction. More specifically, the input interface circuitry 25 inputs various instructions, commands, information, selections, and settings from the operator into the X-ray diagnostic apparatus 1. The fluoroscopy/imaging position is defined by, for example, an angle relative to the isocenter. For example, when the starting point of the first oblique direction (RAO), second oblique direction (LAO), cranial direction (CRA), and caudal direction (CAU) is defined as the fluoroscopy/imaging position and the origin of the three orthogonal axes is defined as the isocenter, the angle of the fluoroscopy/imaging position at the starting point is 0°.

Although not shown, the input interface circuitry 25 is implemented by a trackball, switch button, mouse, keyboard, and the like for, for example, setting a region of interest. The input interface circuitry 25 detects the coordinates of the cursor displayed on a display screen and outputs the detected coordinates to the control circuitry (to be described later). Note that the input interface circuitry 25 may be implemented by a touch panel provided to cover the display screen. In this case, the input interface circuitry 25 detects touched and designated coordinates by a coordinate reading principle such as an electromagnetic induction scheme, electromagnetic distortion scheme, or a pressure-sensitive scheme, and outputs the detected coordinates to the control circuitry 27.

The input interface circuitry 25 converts an input operation received from the operator into an electrical signal. The input interface circuitry 25 outputs the converted electrical signal to the processing circuitry 18, the control circuitry 27, and the like. Note that the input interface circuitry 25 in this specification is not limited to only one including physical components such as a mouse and keyboard. Examples of the input interface circuitry 25 include even electrical signal processing circuitry which receives an electrical signal corresponding to an input operation from an external input device provided separately from the X-ray diagnostic apparatus 1, and outputs the received electrical signal to the processing circuitry 18, the control circuitry 27, and the like.

The input interface circuitry 25 inputs an instruction (to be referred to as an activation instruction hereinafter) concerning activation of a function (to be referred to as a dose distribution generation display function hereinafter) of generating and displaying a simulated dose distribution. The dose distribution generation display function will be described in detail later. After inputting the activation instruction, the input interface circuitry 25 inputs selection of a mode concerning the dose distribution generation display function by the operator. Modes concerning the dose distribution generation display function are, for example, an examination display mode and a playback display mode.

The examination display mode is, for example, a mode in which the moving image of a simulated dose distribution (to be described later) is displayed on an object model together with an X-ray irradiation range during an X-ray examination on an object. When the operator selects the examination display mode via the input interface circuitry 25, the input interface circuitry 25 outputs, to the control circuitry 27, an instruction (to be referred to as an examination display execution instruction hereinafter) to execute the examination display mode.

The playback display mode is a mode in which the moving image of a simulated dose distribution and X-ray irradiation range is displayed again on an object model after an X-ray examination on an object. When the operator selects the playback display mode via the input interface circuitry 25, the input interface circuitry 25 outputs, to the control circuitry 27, an instruction (to be referred to as a playback display execution instruction hereinafter) to execute the playback display mode. When the playback display mode is selected, the input interface circuitry 25 inputs specifying information in accordance with an operator instruction. The input interface circuitry 25 outputs the input specifying information to the control circuitry 27.

The control circuitry 27 includes a CPU (Central Processing Unit) and a memory (neither is shown). The control circuitry 27 temporarily stores, in the memory (not shown), information such as operator instructions, and X-ray irradiation conditions including imaging conditions and fluoroscopy conditions sent from the input interface circuitry 25. The control circuitry 27 controls the high voltage generator 3, the X-ray detector 7, the irradiation range limiter 11, the driving device 17, and the like in order to execute X-ray imaging in accordance with operator instructions, a fluoroscopy/imaging position, X-ray irradiation conditions, and the like which are stored in the memory. The control circuitry 27 controls the high voltage generator 3, the X-ray detector 7, the irradiation range limiter 11, the driving device 17, and the like in order to execute X-ray fluoroscopy in accordance with operator instructions, fluoroscopy conditions, and the like which are stored in the memory.

When the examination display mode is selected via the input interface circuitry 25, the control circuitry 27 outputs X-ray information and geometrical position information to the processing circuitry 18 and the storage circuitry 23. More specifically, the control circuitry 27 outputs X-ray information and position information during an X-ray examination on an object to the storage circuitry 23 in time series at a predetermined time interval. Then, the control circuitry 27 controls the storage circuitry 23 to output the X-ray information and position information stored in the storage circuitry 23 to the processing circuitry 18. As a result, the X-ray information and the position information are output to the processing circuitry 18.

Note that the control circuitry 27 may be read out the dose distribution generation display program stored in the storage circuitry 23, and loads it into the memory. Then the control circuitry 27 controls the storage circuitry 23, the processing circuitry 18, the display circuitry 35, and the like in accordance with the dose distribution generation display program loaded into the memory.

For example, the control circuitry 27 controls the storage circuitry 23 to output X-ray information and position information corresponding to specifying information from the storage circuitry 23 to predetermined circuits in response to input of the specifying information from the input interface circuitry 25. The predetermined units are, for example, the processing circuitry 18 and the display circuitry 35.

More specifically, the control circuitry 27 specifies X-ray information and position information corresponding to the specifying information based on the name and date & time of an X-ray examination, the name and ID of an object, and the like in the specifying information. The control circuitry 27 controls the storage circuitry 23 to output the specified X-ray information and position information from the storage circuitry 23 to the predetermined units. By this control, the specified X-ray information and position information are output from the storage circuitry 23 to the processing circuitry 18, the display circuitry 35, and the like.

The control circuitry 27 controls the storage circuitry 23 to output an object model corresponding to specifying information to predetermined circuits in response to input of the specifying information from the input interface circuitry 25. More specifically, the control circuitry 27 specifies the object model corresponding to the specifying information based on body information such as the weight and height of the object in the specifying information. The control circuitry 27 controls the storage circuitry 23 to output the specified object model from the storage circuitry 23 to predetermined circuits. By this control, the specified object model is output from the storage circuitry 23 to the processing circuitry 18, the display circuitry 35, and the like.

The processing circuitry 18 reads out an edit program 29 corresponding to the edit function from the storage circuitry 23, and executes the readout edit program 29, implementing the edit function. At this time, the processing circuitry 18 functions as an edit unit.

The edit program 29 edits at least one of X-ray information, position information, and an object model displayed by the display circuitry 35 in accordance with an operator instruction via the input interface circuitry 25. For example, the edit function 29 edits at least one of the X-ray information, position information, and object model in accordance with an operator instruction when no X-ray is generated in the X-ray tube 5. The edited X-ray information and position information are output to the irradiation range determination function and the dose distribution generation function. The edited object model is output to the irradiation range determination function, the dose distribution generation function, and the display circuitry 35.

When no necessity of editing at least one of X-ray information, position information, and an object model is input in accordance with an operator instruction via the input interface circuitry 25, the information (X-ray information, position information, or object model) or the like, editing of which is unnecessary, is output in an unedited state to predetermined circuits.

The edit program 29 edits position information based on the difference between an object model before editing and an object model after editing. Also, the edit program 29 edits an area dose (to be referred to as a specifying area dose hereinafter) corresponding to specifying information based on pieces of X-ray information and position information before and after editing, and the dose correspondence table. The edit program 29 outputs the edited area dose (edited specifying area dose) to the dose distribution generation function 33.

When an X-ray examination is executed for a long time, the edit program 29 may edit X-ray information and position information so as to thin them out at a predetermined time interval. When an X-ray examination is executed for a long time, the edit program 29 may edit X-ray information and position information so as to average them at a predetermined time interval. The edit program 29 may edit position information and X-ray information corresponding to the still period of the support frame 9 so as to thin them out. That is, the edit function 29 can properly compress data (X-ray information and position information) in accordance with an operator instruction for the X-ray information and the position information.

The processing circuitry 18 reads out an irradiation range determination program 31 corresponding to the irradiation range determination function from the storage circuitry 23, and executes the readout irradiation range determination program 31, implementing the irradiation range determination function. At this time, the processing circuitry 18 functions as an irradiation range determination unit.

The irradiation range determination program 31 determines a plurality of X-ray irradiation ranges in time series based on position information and X-ray information, at least either of which has been edited. More specifically, the irradiation range determination program 31 determines a plurality of X-ray irradiation ranges and a plurality of irradiation areas on an object model corresponding to the body surface of an object in time series in an X-ray examination based on a limited irradiation range in the X-ray information, and a relative positional relationship and the position of the top plate 151 in the position information.

That is, the irradiation range determination program 31 determines each of the plurality of X-ray irradiation ranges for every movement of the support frame 9 and top plate 151. The irradiation range determination program 31 outputs the plurality of X-ray irradiation ranges in time series to the display circuitry 35. The irradiation range determination program 31 outputs the irradiation areas to the dose distribution generation function 33.

The processing circuitry 18 reads out a dose distribution generation program 33 corresponding to the dose distribution generation function from the storage circuitry 23, and executes the readout dose distribution generation program 33, implementing the dose distribution generation function. At this time, the processing circuitry 18 functions as a dose distribution generation unit.

The dose distribution generation program 33 generates a plurality of simulated dose distributions in time series based on position information and X-ray information, at least either of which has been edited. More specifically, based on the result of editing at least either of X-ray information and position information concerning the first dose distribution corresponding to exposure of an object along with generation of X-rays, the dose distribution generation program 33 generates the second dose distribution, which is a simulation result, as the simulated dose distribution without generating X-rays. In other words, the dose distribution generation program 33 calculates (simulates) a simulated dose distribution by using the result of editing at least either of X-ray information and position information.

More specifically, the dose distribution generation program 33 calculates an air kerma at the reference position in time series in an X-ray examination based on the area dose (measured or edited area dose) and the type (thickness) of a radiation quality adjustment filter in the X-ray information, and the relative positional relationship, the position of the top plate 151, the reference position, and the SID in the position information.

Then, the dose distribution generation program 33 determines a plurality of incident skin doses on an object model corresponding to the body surface of an object in time series in the X-ray examination based on the calculated air kerma, the irradiation area, and the relative positional relationship and the position of the top plate 151 in the position information.

When calculating an incident skin dose from the air kerma, the dose distribution generation program 33 can calculate it in consideration of the influence of back scattered radiation. The dose distribution generation program 33 generates a simulated dose distribution by mapping an incident skin dose at an X-ray irradiation position on the surface of an object model.

For example, the dose distribution generation program 33 determines each of a plurality of simulated dose distributions for every predetermined time interval. Note that the dose distribution generation program 33 may generate a simulated dose distribution using an area dose measured in advance, the dose correspondence table, and the like. The dose distribution generation program 33 outputs a plurality of simulated dose distributions in time series to the display circuitry 35.

The display circuitry 35 displays a projection image generated by the image generation program 19 on the display 351. The display circuitry 35 displays, on the display 351, an input screen concerning input of a fluoroscopy/imaging position, X-ray irradiation conditions, and the like.

The display circuitry 35 displays, on the display 351, X-ray information, position information, and an object model corresponding to specifying information in response to input of the specifying information.

In the playback display mode, the display circuitry 35 displays in time series a plurality of superimposed images in each of which a simulated dose distribution and an X-ray irradiation range are superimposed in time series on a dose distribution display model (object model or shape model). That is, the display circuitry 35 sequentially superimposes and displays simulated dose distributions on the object model. Note that the image generation program 19 may generate a superimposed image concerning a simulated dose distribution.

More specifically, when the playback display mode is selected, a plurality of superimposed images in time series concerning a past X-ray examination are generated based on X-ray information and position information. The display circuitry 35 displays the moving image of the newly generated superimposed images in time series. At this time, the edit function 29 may properly edit the X-ray information, position information, and an object model concerning the past X-ray examination.

In other words, when no X-ray is generated, the display circuitry 35 sequentially superimposes and displays simulated dose distributions relative to an object in time series on an object model. When the object model is edited, the display circuitry 35 sequentially superimposes and displays simulated dose distributions on the edited object model.

In the examination display mode, the display circuitry 35 displays in time series the moving image of a plurality of superimposed images in time series during an X-ray examination on an object.

(Dose Distribution Generation Display Function)

The dose distribution display function according to this embodiment will be explained. FIG. 6 is a block diagram showing the association between circuits regarding the dose distribution display function.

(Examination Display Mode)

When the examination display mode is selected in accordance with an operator instruction via the input interface circuitry 25, the control circuitry 27 outputs X-ray information and position information to the storage circuitry 23 and the processing circuitry 18 at a predetermined time interval during an X-ray examination (A1 and A2 in FIG. 6).

In addition, the control circuitry 27 specifies an object model corresponding to body information such as the weight and height of an object. The control circuitry 27 controls the storage circuitry 23 to output the specified object model from the storage circuitry 23 to the display circuitry 35 (A2 in FIG. 6).

The irradiation range determination program 31 generates an X-ray irradiation range and an irradiation area based on the X-ray information and position information input from the control circuitry 27. The irradiation range determination program 31 outputs the determined X-ray irradiation range to the display circuitry 35. The irradiation range determination program 31 outputs the determined irradiation area to the dose distribution generation function 33.

The dose distribution generation program 33 generates a simulated dose distribution based on the X-ray information and position information input from the control circuitry 27, the calculated irradiation area, and the measured area dose. The dose distribution generation program 33 outputs the generated simulated dose distribution to the display circuitry 35.

The display circuitry 35 updates the superimposed image, in which the simulated dose distribution and the irradiation range are superimposed on the object model, at a predetermined time interval during the X-ray examination, and displays the superimposed image as a moving image on the display 351.

(Playback Display Mode)

When the playback display mode is selected in accordance with an operator instruction via the input interface circuitry 25 and specifying information is input, the control circuitry 27 controls the storage circuitry 23 to output X-ray information, position information, and an object model corresponding to the specifying information to the edit function 29 of the processing circuitry 18 and the display circuitry 35 (A2 in FIG. 6).

When no necessity of editing at least one of the X-ray information, position information, and object model corresponding to the specifying information is input, the information or the like, editing of which is unnecessary, is output to the processing circuitry 18 and the display circuitry 35 (B1 and B2 in FIG. 6).

The storage circuitry 23 outputs the X-ray information, position information, and object model corresponding to the specifying information to the display circuitry 35 under the control of the control circuitry 27 (B1 in FIG. 6). At this time, the displayed X-ray information, position information, and object model change to a state in which they can be edited by the edit program 29. The X-ray information, position information, and object model edited via the input interface circuitry 25 and the edit program 29 are output to the irradiation range determination function and dose distribution generation function of the processing circuitry 18 (B2 in FIG. 6). The storage circuitry 23 outputs the area dose corresponding to the specifying information to the dose distribution generation function (B2 in FIG. 6).

When at least one of the X-ray information, position information, and object model is edited, the edit program 29 edits the specified area dose based on the edited information (X-ray information or position information) and the dose correspondence table. The edit program 29 outputs the edited area dose to the dose distribution generation function 33. The edit program 29 may select an object model different from one at the time of an examination in accordance with an operator instruction via the input interface circuitry 25. The edit program 29 may select and edit an object model in a posture different from one at the time of an examination in accordance with an operator instruction via the input interface circuitry 25, in order to change the posture of the object model.

The irradiation range determination program 31 determines a plurality of irradiation ranges and a plurality of irradiation areas in time series based on edited or unedited X-ray information and position information. The irradiation range determination program 31 outputs the plurality of irradiation ranges in time series to the display circuitry 35. The irradiation range determination program 31 outputs the plurality of irradiation areas in time series to the dose distribution generation program 33.

The dose distribution generation program 33 generates a plurality of simulated dose distributions in time series based on edited or unedited X-ray information and position information. The dose distribution generation program 33 outputs the plurality of generated simulated dose distributions to the display circuitry 35.

The display circuitry 35 displays, as a moving image in time series on the display 351, a plurality of superimposed images in each of which the simulated dose distribution and the irradiation range are superimposed in time series on the edited or unedited object model.

(Processing Sequence of Dose Distribution Generation Display Function)

Figure 7:
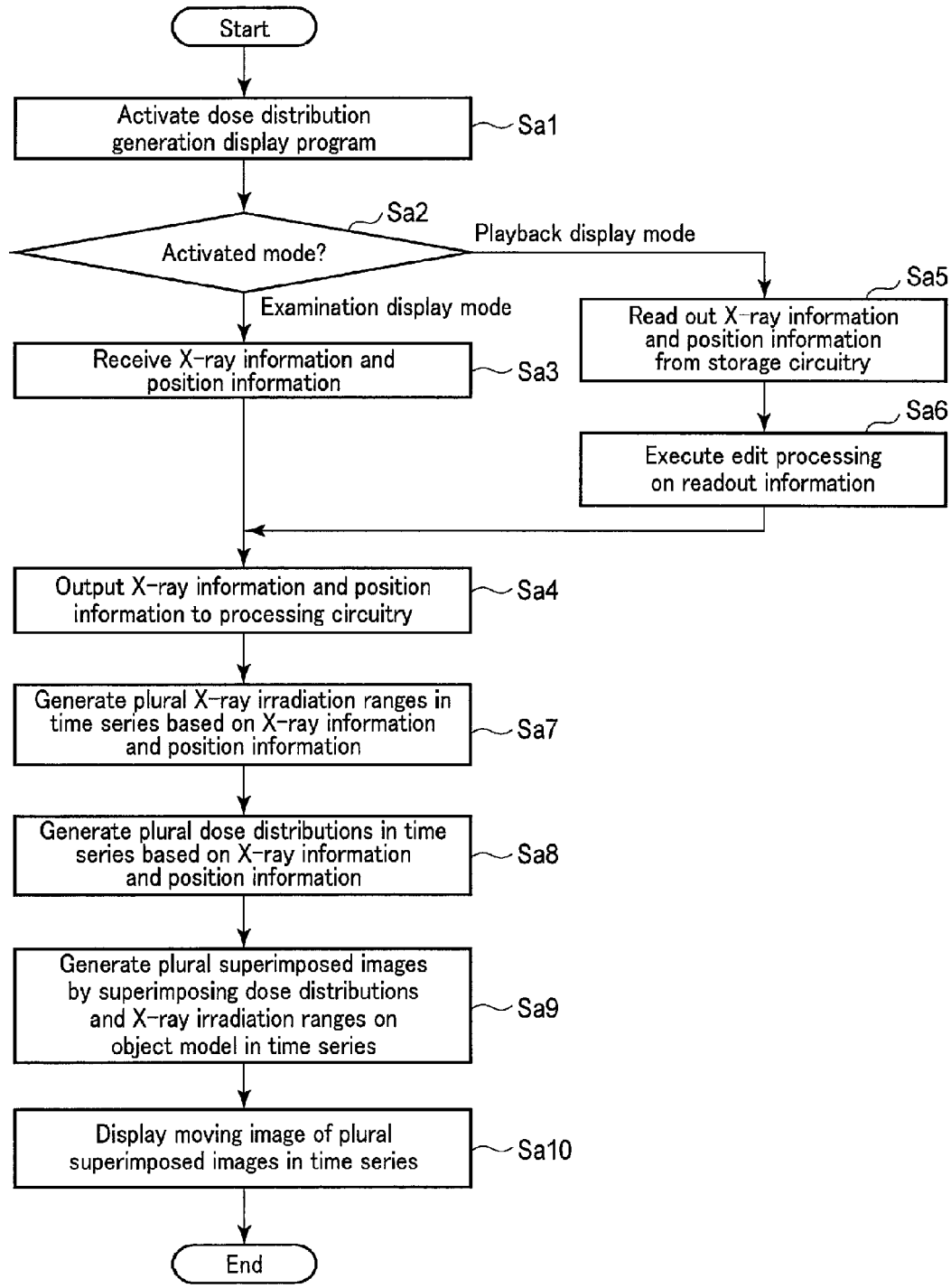
FIG. 7 is a flowchart showing an example of a procedure for processing regarding the dose distribution generation display function according to this embodiment.

FIG. 7 is a flowchart showing an example of a procedure for processing (to be referred to as dose distribution generation display processing hereinafter) regarding the dose distribution generation display function.

The dose distribution generation display function is activated in accordance with an operator instruction via the input interface circuitry 25 (step Sa1). A mode concerning the dose distribution generation display function is input in accordance with an operator instruction via the input interface circuitry 25 (step Sa2). If the examination display mode is input, an X-ray examination on an object is executed. During the X-ray examination, X-ray information and position information are received from the control circuitry 27 and the like at a predetermined time interval (step Sa3). The received X-ray information and position information are output to the processing circuitry 18 (step Sa4).

If the playback display mode is input, specifying information is input in accordance with an operator instruction via the input interface circuitry 25. X-ray information, position information, and an object model corresponding to the input specifying information are read out from the storage circuitry 23 (step Sa5). At this time, the readout X-ray information, position information, and object model are output to the processing circuitry 18 and the display circuitry 35. Edit processing is executed on the X-ray information, position information, and object model displayed on the display 351 by the display circuitry 35 (step Sa6).

Figure 8:
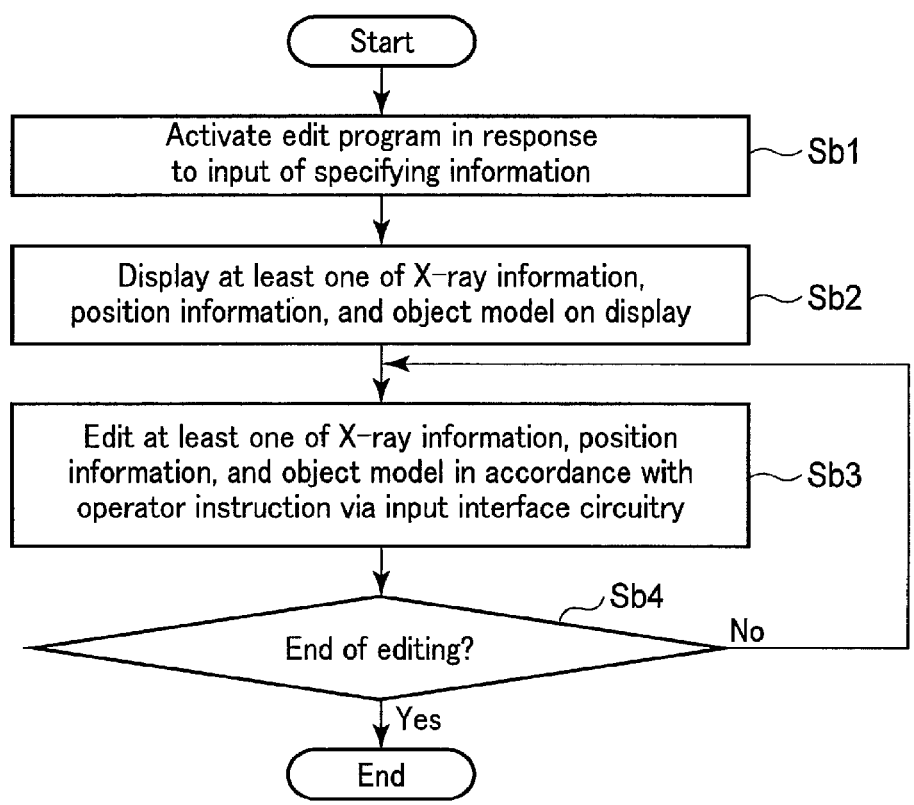
FIG. 8 is a flowchart showing an example of a procedure for the function of edit processing according to this embodiment.

FIG. 8 is a flowchart showing an example of a procedure for the function (edit program 29) of edit processing of editing at least one of X-ray information, position information, and an object model corresponding to specifying information. The edit program 29 is activated in response to input of specifying information (step Sb1). At least one of X-ray information, position information, and an object model corresponding to the specifying information is displayed on the display 351 by the display circuitry 35 (step Sb2).

The edit program 29 edits at least one of the X-ray information, position information, and object model corresponding to the specifying information in accordance with an operator instruction via the input interface circuitry 25 (step Sb3). After the end of editing (step Sb4), the unedited or edited X-ray information, position information, and object model are output to the irradiation range determination function and dose distribution generation function of the processing circuitry 18 (step Sa4).

A plurality of X-ray irradiation ranges and irradiation areas in time series are generated based on the X-ray information and the position information (step Sa7). A plurality of simulated dose distributions in time series are generated (calculated) based on the X-ray information and the position information (step Sa8). That is, a plurality of simulated dose distributions in time series are simulated based on the X-ray information and the position information.

The simulated dose distributions and the X-ray irradiation ranges are superimposed in time series on the object model, generating a plurality of superimposed images (step Sa9). The moving image of the plurality of superimposed images is displayed in time series (step Sa10).

Figure 9:
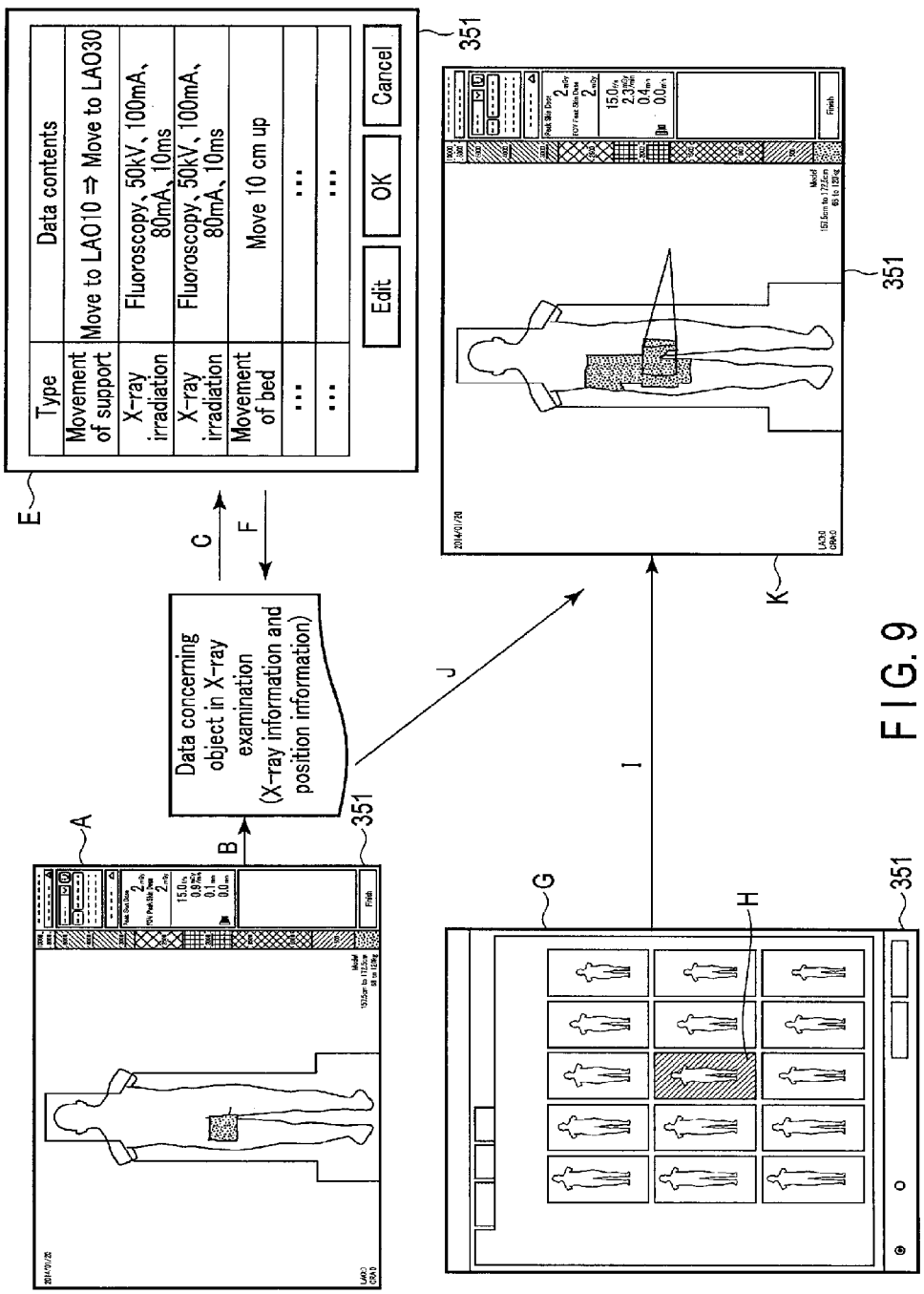
FIG. 9 is a view showing an example of displaying the moving image of a simulated dose distribution on the display by using position information edited by edit processing according to this embodiment.

FIG. 9 is a view showing an example of displaying the moving image of a simulated dose distribution on the display 351 by using position information edited by edit processing. A in FIG. 9 represents a simulated dose distribution displayed during an X-ray examination (examination display mode). Data (X-ray information and position information) concerning an object in the X-ray examination are saved in the storage circuitry 23 (B in FIG. 9). When the playback display mode is selected after the X-ray examination, the X-ray information and the position information are read out from the storage circuitry 23 (C in FIG. 9).

E in FIG. 9 represents the X-ray information and position information displayed on the display 351 by the display circuitry 35 in edit processing. E in FIG. 9 represents a state in which "LAO10" is edited to "LAO30" in a type "movement of support" in the position information.

By reflecting an edit result by the edit program 29, for example, new position information is generated and stored in the storage circuitry 23 (F in FIG. 9). In FIG. 9, the object model is not edited. That is, the object model has not been changed, as represented by G in FIG. 9 (H in FIG. 9). The unedited object model is output to the display circuitry 35 (I in FIG. 9). A plurality of simulated dose distributions and a plurality of X-ray irradiation ranges in time series are generated using the unedited X-ray information and the edited position information (J in FIG. 9).

The generated simulated dose distributions and X-ray irradiation ranges are superimposed in time series on the unedited object model, generating a plurality of superimposed images in time series. The plurality of superimposed images are displayed in time series (moving image display: K in FIG. 9). The simulated dose distributions in A and K of FIG. 9 are represented by gradation in accordance with the magnitude of the patient skin dose. In practice, however, the simulated dose distributions are displayed in different hues in accordance with the magnitude of the patient skin dose.

Figure 10:
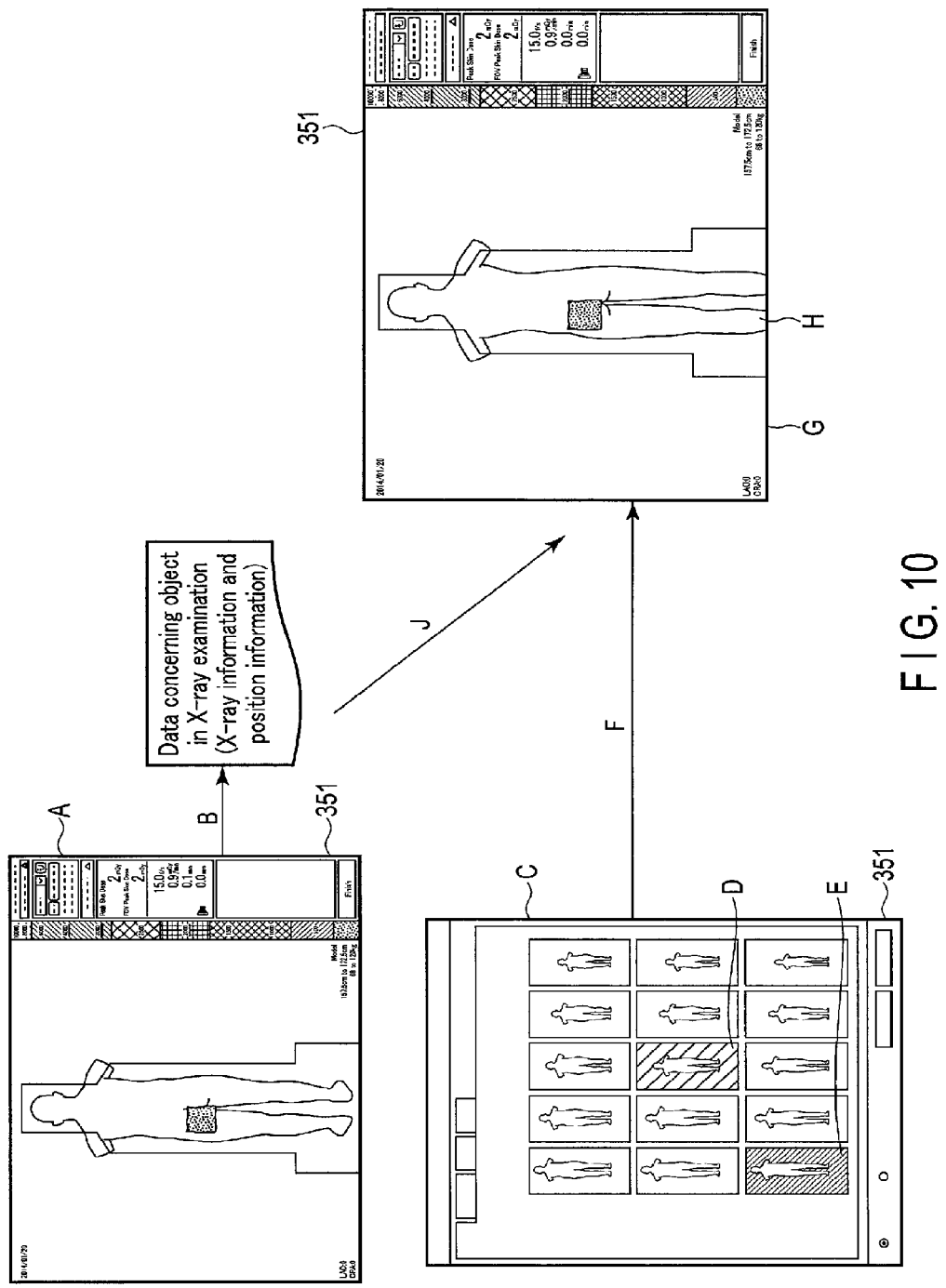
FIG. 10 is a view showing an example of displaying, on the display, the moving image of a simulated dose distribution calculated (simulated) using an object model edited by edit processing according to this embodiment.

FIG. 10 is a view showing an example of displaying, on the display 351, the moving image of a simulated dose distribution calculated (simulated) using an object model edited by edit processing. A in FIG. 10 represents a simulated dose distribution displayed during an X-ray examination (examination display mode). Data (X-ray information and position information) concerning an object in the X-ray examination are saved in the storage circuitry (B in FIG. 10). When the playback display mode is selected after the X-ray examination, a list of object models including an object model corresponding to specifying information is read out from the storage circuitry 23 (C in FIG. 10). At this time, the list of object models is displayed by the display circuitry 35.

In the displayed list of object models, the object model corresponding to the specifying information is displayed by, for example, a predetermined highlight (e.g., hatching or hue), as represented by D in FIG. 10. E in FIG. 10 represents the edited (changed) object model in accordance with an operator instruction. The edited object model is output to the display circuitry 35 (F in FIG. 10). At this time, the position information may be edited in accordance with body information of the edited object model.

A plurality of simulated dose distributions and a plurality of X-ray irradiation ranges in time series are generated (simulated) based on the edited position information and X-ray information. The generated simulated dose distributions and X-ray irradiation ranges are superimposed in time series on the edited object model, generating a plurality of superimposed images in time series. The plurality of superimposed images are displayed in time series (moving image display: G in FIG. 10).

H in FIG. 10 represents the edited object model. The simulated dose distributions in A and G of FIG. 10 are represented by gradation in accordance with the magnitude of the patient skin dose. In practice, however, the simulated dose distributions are displayed in different hues in accordance with the magnitude of the patient skin dose.

When a cylindrical shape as represented by Cy in FIG. 4 is used as a dose distribution model, the simulated dose distribution DS3 is represented by gradation in accordance with the magnitude of the patient skin dose. In practice, however, the simulated dose distribution DS3 is displayed in different hues in accordance with the magnitude of the patient skin dose.

When a spherical shape as represented by Sp in FIG. 5 is used as a dose distribution model, the simulated dose distributions DS4 and SD5 are represented by gradation in accordance with the magnitude of the patient skin dose. In practice, however, the simulated dose distributions DS4 and DS5 are displayed in different hues in accordance with the magnitude of the patient skin dose.

(First Modification)

The first modification is different from the embodiment in that the support frame 9, the bed 15, the top plate 151, and the like are moved (to be referred to as a moving operation reproduction function hereinafter) together with the moving image display of superimposed images by using position information stored in the storage circuitry 23 or edited position information.

The input interface circuitry 25 inputs a moving operation reproduction function start instruction (to be referred to as an operation reproduction instruction hereinafter) in accordance with an operator instruction. The input interface circuitry 25 inputs specifying information in accordance with an operator instruction in order to specify position information concerning the moving operation reproduction function. The input interface circuitry 25 outputs the operation reproduction instruction and specifying information to the control circuitry 27.

In response to the input of the operation reproduction instruction and specifying information, the control circuitry 27 reads out position information corresponding to the specifying information from the storage circuitry 23. Note that the readout position information may be properly edited via the edit program 29 and the input interface circuitry 25. The control circuitry 27 controls the driving device 17 to drive the support frame 9, the bed 15, the top plate 151, and the like in accordance with the readout position information.

The driving device 17 drives the support frame 9, the bed 15, and the top plate 151 in accordance with the position information under the control of the control circuitry 27. By driving the support frame 9, the bed 15, and the top plate 151 by the driving device 17, a moving operation corresponding to the position information is reproduced.

(Moving Operation Reproduction Function)

The moving operation reproduction function is a function of reproducing the moving operation of the support frame 9, bed 15, and top plate 151 in a past X-ray examination based on stored position information. Processing (to be referred to as moving operation reproduction processing hereinafter) concerning the moving operation reproduction function will be described below.

FIG. 11 is a flowchart showing an example of a procedure for moving operation reproduction processing.

An operation reproduction instruction is input in accordance with an operator instruction via the input interface circuitry 25 (step Sc1). Then, specifying information for specifying position information to be used in the moving operation reproduction function is input.

Position information corresponding to the specifying information is specified based on the specifying information. The specified position information is read out from the storage circuitry 23 (step Sc2). The support frame 9, the bed 15, and the top plate 151 are driven in accordance with the readout position information (step Sc3). A plurality of superimposed images corresponding to the specifying information are displayed in time series, and the support frame 9, the bed 15, and the top plate 151 are moved.

(Second Modification)

The second modification is different from the embodiment and the first modification in that a direction from a viewpoint toward an object model is set as a line-of-sight direction based on the relative positional relationship between the line of sight and the object model in response to input of the viewpoint concerning display of simulated dose distributions, and simulated dose distributions are sequentially superimposed and displayed on the object model.

The input interface circuitry 25 inputs a viewpoint concerning display of simulated dose distributions in accordance with an operator instruction. The input interface circuitry 25 outputs viewpoint information concerning the input viewpoint to the processing circuitry 18. The viewpoint information is, for example, information representing the position of the viewpoint.

The storage circuitry 23 stores a display control program concerning a display control function. The display control function will be described in detail later. The storage circuitry 23 outputs the display control program to the processing circuitry 18 in response to input of a viewpoint via the input interface circuitry 25.

The processing circuitry 18 reads out the display control program from the storage circuitry 23 in response to input of the viewpoint via the input interface circuitry 25. The processing circuitry 18 executes the readout display control program, implementing the display control function (not shown). At this time, the processing circuitry 18 functions as a display control unit.

The display control program determines the relative positional relationship between the position of an input viewpoint and an object model. The relative positional relationship includes, for example, the distance between the viewpoint and the object model, and the line-of-sight direction from the viewpoint toward the object model. The display control program determines the orientation (to be referred to as a model direction hereinafter) of the object model relative to the line-of-sight direction based on the relative positional relationship. The model direction is, for example, an angle indicating the orientation of the object relative to the top plate 151.

Based on the determined model direction and line-of-sight direction, the display control program determines the superimposition position and superimposition shape of a simulated dose distribution in the object model corresponding to the model direction. The display control program outputs the model direction, the superimposition position, and the superimposition shape to the display circuitry 35.

Note that the edit program 29 may edit the model direction and the superimposition position and superimposition shape of a simulated dose distribution. Alternatively, the irradiation range determination program 31 may determine the superimposition position and superimposition shape of a simulated dose distribution. The dose distribution generation program 33 may calculate again (simulate again) a simulated dose distribution corresponding to a superimposition position and a superimposition shape.

The display circuitry 35 sets a direction from the viewpoint toward the object model as the line-of-sight direction in accordance with the relative positional relationship between the viewpoint and the object model, and sequentially superimposes and displays simulated dose distributions on the object model. For example, when the object model is volume data, the display circuitry 35 rotates the object model in accordance with the determined model direction, and displays the object model on the display 351.

When the object model is two-dimensional data, the display circuitry 35 reads out an object model corresponding to the determined model direction from the storage circuitry 23, and displays the readout object model on the display 351.

Figure 12:
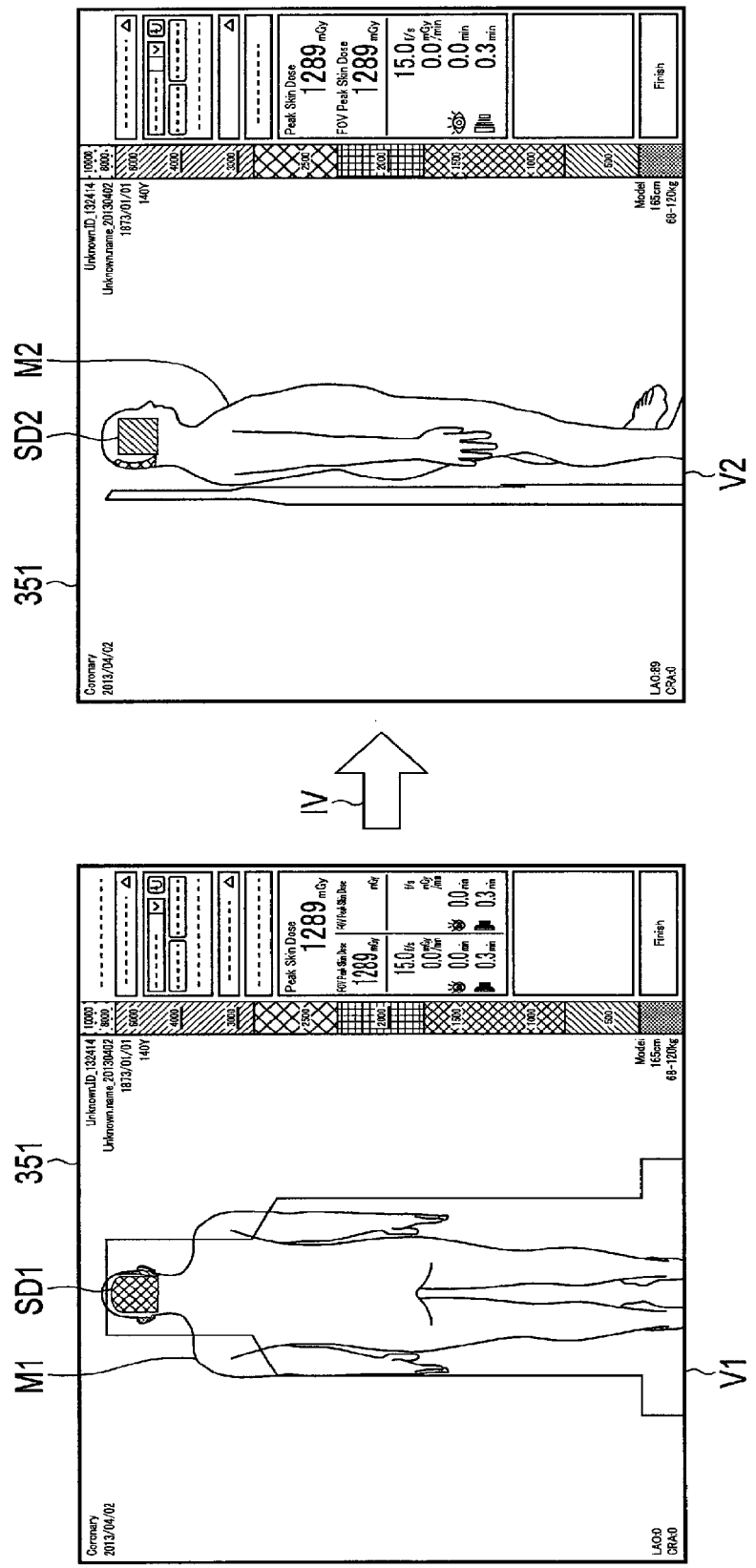
FIG. 12 is a view showing an example of sequentially superimposing simulated dose distributions on an object model and displaying them on the display before and after inputting a viewpoint according to the second modification of this embodiment.

The display circuitry 35 sequentially superimposes and displays simulated dose distributions on the object model corresponding to the model direction in accordance with the determined superimposition position and superimposition shape. FIG. 12 is a view showing an example of sequentially superimposing simulated dose distributions on an object model and displaying them on the display 351 before and after inputting a viewpoint.

V1 in FIG. 12 is a view showing an example of sequentially superimposing a simulated dose distribution SD1 on an object model M1 and displaying it on the display 351 before inputting a viewpoint via the input interface circuitry 25. An arrow IV in FIG. 12 indicates input of a viewpoint. In FIG. 12, the viewpoint is assumed to be input in the right-hand direction (side surface) of the object model.

V2 in FIG. 12 is a view showing an example of sequentially superimposing a simulated dose distribution SD2 on an object model M2 corresponding to a model direction, and displaying it on the display 351 in accordance with a determined superimposition position and superimposition shape after inputting a viewpoint via the input interface circuitry 25. As is apparent from V1 and V2 in FIG. 12, the orientation of the object model and the superimposition position and shape of the simulated dose distribution are changed in accordance with the line-of-sight direction in accordance with the line-of-sight direction in response to input of the viewpoint in the second modification.

The above-described arrangement can obtain the following effects.

The X-ray diagnostic apparatus 1 according to this embodiment can generate a plurality of simulated dose distributions in time series based on stored X-ray information and position information, and determine a plurality of X-ray irradiation ranges in time series. Further, the X-ray diagnostic apparatus 1 can generate a plurality of superimposed images in each of which the generated simulated dose distribution and the determined X-ray irradiation range are superimposed in time series on the object model, and sequentially display the moving image of the plurality of generated superimposed images in time series.

In addition, the X-ray diagnostic apparatus 1 according to this embodiment can edit (change) the stored X-ray information, position information, and object model in accordance with an operator instruction, superimpose the simulated dose distributions and the X-ray irradiation ranges on the object model in accordance with the edited X-ray information, position information, and object model, and display them as a moving image.

Hence, the X-ray diagnostic apparatus 1 according to this embodiment can reproduce, as a moving image display, a change of the simulated dose distribution and a change of the X-ray irradiation range in the course of an X-ray examination without saving, as a moving image, a distribution change of the exposure during a past examination. That is, the X-ray diagnostic apparatus 1 according to this embodiment can reproduce (play back) a change of the dose distribution and a change of the X-ray irradiation range during the X-ray examination, and can also simulate an X-ray examination.

Further, the edit function according to this embodiment can play back in a short time a change of the dose distribution and a change of the X-ray irradiation range in a long-time X-ray examination. In addition, the edit function according to this embodiment can edit X-ray information and position information in order to reduce the exposure of an object. The X-ray diagnostic apparatus 1 can contribute to further reduction of the exposure by simulating an X-ray examination using the edited X-ray information and position information.

The X-ray diagnostic apparatus 1 according to the first modification of this embodiment can reproduce the moving operation of the support frame 9, bed 15, and top plate 151 based on position information. The operator can reproduce (play back) a change of the dose distribution and a change of the X-ray irradiation range during the X-ray examination, and can simulate the moving operation of the support frame 9, bed 15, and top plate 151 in the X-ray examination.

According to the second modification of this embodiment, simulated dose distributions corresponding to a line-of-sight direction can be superimposed on an object model corresponding to the line-of-sight direction in response to input of a viewpoint via the input interface circuitry 25, and can be displayed as a moving image. That is, according to this modification, simulated dose distributions viewed from an arbitrary viewpoint desired by the operator can be sequentially superimposed and displayed on an object model rotated in accordance with the line-of-sight direction. According to this embodiment, the operator can confirm the moving image display of simulated dose distributions serving as dose distribution simulation results not only in a direction from the position of the X-ray focus toward the object model but also in an arbitrary direction.

Therefore, the X-ray diagnostic apparatus 1 according to this embodiment allows, for example, an operator in charge of training to execute training in reducing exposure of an object and simulation of an examination while changing conditions concerning the dose distribution and the X-ray irradiation range into various conditions. Further, X-ray information and position information acquired during an X-ray examination can be effectively used.

As still another modification of this embodiment, when the technical idea of the X-ray diagnostic apparatus 1 is implemented by a dose distribution display apparatus 10, the dose distribution display apparatus 10 includes, for example, the constituent elements surrounded by a chain line in the block diagram of FIG. 1. At this time, the dose distribution display apparatus 10 executes various functions such as the dose distribution generation display function shown in FIG. 7 and the edit function shown in FIG. 8 according to this embodiment in the same way as in this embodiment.

In addition, the functions according to this embodiment and the modifications can be implemented by installing programs (dose distribution generation display program and the like) for executing various processes such as dose distribution generation display processing and edit processing in a computer such as a workstation and loading them into the memory. At this time, the programs which can cause the computer to execute the method can be distributed by storing them in storage media such as magnetic disks (Floppy® disks, hard disks, and the like), optical disks (CD-ROMs, DVDs, and the like), and semiconductor memories.

Note that each circuitry according to this embodiment may be constituted by one or a plurality of electronic circuits. In the above description, the single processing circuitry 18 executes various functions such as the image generation program 19, the edit program 29, the irradiation range determination program 31, and the dose distribution generation program 33. Alternatively, a plurality of independent processors may be combined to constitute the processing circuitry, and the processors may execute programs to implement various functions. The image generation program 19, the edit program 29, the irradiation range determination program 31, and the dose distribution generation program 33 may be implemented by different processing circuits, respectively.

The word "processor" used in the above description means circuitry such as a CPU, a GPU (Graphics Processing Unit), an MPU (Micro Processing Unit), an ASIC (Application Specific Integrated Circuit), a programmable logic device (e.g., an SPLD (Simple Programmable Logic Device), a CPLD (Complex Programmable Logic Device), or an FPGA (Field Programmable Gate Array)), or the like.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A dose distribution display apparatus comprising:
    storage circuitry configured to store, in a time series in an X-ray examination, position information of a support frame which supports an X-ray tube, and store, in the time series in the X-ray examination, X-ray irradiation conditions concerning X-rays generated by the X-ray tube;
    processing circuitry configured to
        edit at least one of the X-ray irradiation conditions and the position information concerning a first dose distribution corresponding to exposure of an object along with generation of the X-rays in the X-ray examination in accordance with an operator instruction, and
        simulate a plurality of second dose distributions in time series using the X-ray irradiation conditions and the position information without generating the X-rays, at least one of which has been edited; and
    display circuitry configured to sequentially superimpose and display the second dose distributions on an object model.

2. The apparatus according to claim 1, wherein
    the processing circuitry is configured to edit at least one of the X-ray irradiation conditions and the position information in accordance with the operator instruction when the X-rays are not generated in the X-ray tube, and
    the display circuitry is configured to sequentially superimpose and display the second dose distributions of the object on the object model in time series when the X-rays are not generated.

3. The apparatus according to claim 1, wherein
    the processing circuitry is configured to edit the object model in accordance with the operator instruction, and
    the display circuitry is configured to sequentially superimpose and display the second dose distributions on the edited object model.

4. The apparatus according to claim 3, wherein the processing circuitry is configured to edit the position information based on a difference between an object model after editing and an object model before editing.

5. The apparatus according to claim 1, further comprising input interface circuitry configured to input a viewpoint concerning display of the second dose distributions, wherein
    the display circuitry is configured to
        set a direction from the viewpoint toward the object model as a line-of-sight direction based on a relative positional relationship between the viewpoint and the object model, and
        sequentially superimpose and display the second dose distributions on the object model.

6. An X-ray diagnostic apparatus comprising:
    an X-ray tube configured to irradiate an object with X-rays;
    storage circuitry configured to store, in a time series in an X-ray examination, position information of a support frame which supports the X-ray tube, and store, in the time series in the X-ray examination, X-ray irradiation conditions concerning the X-rays generated by the X-ray tube;
    processing circuitry configured to
        edit at least one of the X-ray irradiation conditions and the position information concerning a first dose distribution corresponding to exposure of an object along with generation of the X-rays in the X-ray examination in accordance with an operator instruction, and
        simulate a plurality of second dose distributions in time series using the X-ray irradiation conditions and the position information without generating the X-rays, at least one of which has been edited; and
    display circuitry configured to sequentially superimpose and display the second dose distributions on an object model.

7. The apparatus according to claim 6, further comprising control circuitry configured to control movement of the support frame based on the position information.

* * * * *